United States Patent [19]

McCall

[11] 4,166,853
[45] Sep. 4, 1979

[54] ANTIHYPERTENSIVE 7-TRIFLUOROMETHYL-4-AMINOQUINO-LONES

[75] Inventor: John M. McCall, Kalamazoo, Mich.

[73] Assignee: The Upjohn Company, Kalamazoo, Mich.

[21] Appl. No.: 903,088

[22] Filed: May 5, 1978

[51] Int. Cl.² .................... A61K 31/47; C07D 215/44
[52] U.S. Cl. ...................................... 424/258; 546/161
[58] Field of Search ................ 260/287 AR; 424/258; 546/161

[56] References Cited

U.S. PATENT DOCUMENTS

| | | | |
|---|---|---|---|
| 3,632,761 | 1/1972 | Graham et al. ............... | 260/287 AR |
| 3,875,165 | 4/1975 | Archibald et al. ............ | 260/287 AR |
| 3,971,787 | 7/1976 | Archibald et al. ............ | 260/287 AR |
| 4,025,629 | 5/1977 | Coverdale .................... | 260/287 AR |

OTHER PUBLICATIONS

March, Advanced Org. Chem., pp. 335-339, (1968).
Morrison et al., Org. Chem., (1966), pp. 590-591.

*Primary Examiner*—David Wheeler
*Attorney, Agent, or Firm*—Robert A. Armitage

[57] ABSTRACT

Antihypertensive compounds of the formula II

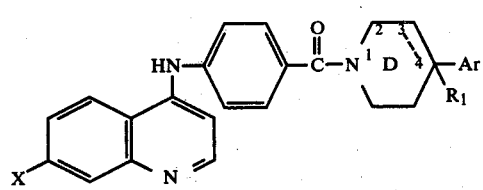

wherein D is a piperidino or 1,2,5,6-tetrahydropyridino ring; wherein X is chloro or trifluoromethyl; wherein $R_1$ is hydrogen or hydroxy when the D ring is piperidino, or nothing when the D ring is 1,2,5,6-tetrahydropyridino; and, wherein the moiety Ar is 2-oxo-1-benzimidazolinyl, phenyl, or phenyl substituted by one or two halo, trifluoromethyl, or alkyl, alkoxy, in which the carbon moieties are of 1 to 3 carbon atoms, inclusive, and halo is chloro, bromo, or fluoro, are produced by reacting 4-[[7-(chloro) or (trifluoromethyl)-4-quinolinyl]-amino]benzoic acid with thionyl chloride or a carbonyl diimidazole and subsequent reaction with the selected substituted piperidine or 1,2,5,6-tetrahydropyridine.

The pharmacologically acceptable acid addition salts of II can also be used as antihypertensives.

30 Claims, No Drawings

ANTIHYPERTENSIVE 7-TRIFLUOROMETHYL-4-AMINOQUINOLONES

BRIEF SUMMARY OF THE INVENTION

Field of the Invention

This invention concerns new organic compounds and in particular, 4-quinolinylaminobenzoylpiperidines of formula II, their use as antihypertensives in mammals, including humans, and their formulations for that use.

The new compounds and the processes of this invention can be illustratively represented by the following schemes:

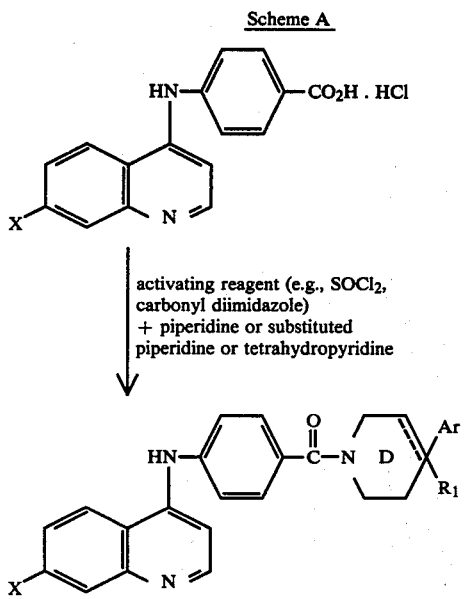

wherein D is a piperidino or 1,2,5,6-tetrahydropyridino ring; wherein X is chloro or trifluoromethyl; wherein $R_1$ is hydrogen or hydroxy when the D-ring is piperidino, or nothing when the D-ring is 1,2,5,6-tetrahydropyridino; and, wherein the Ar is 2-oxo-1-benzimidazolinyl, phenyl, or phenyl substituted by one or two halo, trifluoromethyl, alkyl or alkoxy, in which the carbon moieties are from 1 to 3 carbon atoms, inclusive, and halo is chloro, bromo, or fluoro.

This invention also encompasses the pharmacologically acceptable acid addition salts of the compounds of the formula II.

The process of this invention comprises the conversion of a 7-substituted 4-quinolinylaminobenzoic acid to its acid chloride with thionyl chloride or to its imidazolide with carbonyl diimidazole and treating the intermediate with the selected piperidine or 1,2,5,6-tetrahydropyridine.

PREFERRED EMBODIMENT OF THE INVENTION

The alkyl groups in this invention, having 1 to 3 carbon atoms, inclusive, comprise methyl, ethyl, propyl, isopropyl, with methyl preferred.

The halogens are chloro, bromo, and fluoro, with chloro and fluoro preferred.

The pharmacologically acceptable salts of compound of the formula II comprise the hydrochlorides, hydrobromides, hydriodides, sulfates, phosphates, cyclohexanesulfamates, pamoates, methanesulfonates, and the like, prepared by reacting a compound of formula II with the stoichiometrically calculated amount of the selected pharmacologically acceptable acid.

The preferred compounds of this invention are selected from the group consisting of the compounds of the formula IIA

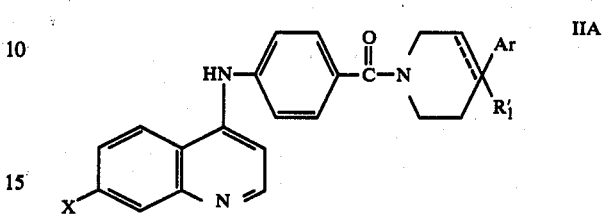

wherein X is chloro or trifluoromethyl; wherein the D-ring is piperidino, $R'_1$ is hydroxy, and Ar is phenyl substituted by one or two halo, alkyl, alkoxy in which halo is chloro or fluoro, and alkyl and alkoxy are of 1 to 3 carbon atoms, inclusive, or trifluoromethyl; or the D-ring is 1,2,5,6-tetrahydropyridine, $R'_1$ is nothing and Ar is phenyl or phenyl substituted with one or two halo, alkyl, alkoxy or trifluoromethyl groups, in which halo, alkyl and alkoxy are defined as above, or the pharmacologically acceptable acid addition salts thereof.

The most preferred compounds of this invention are selected from the group consisting of the compounds of the formula IIB

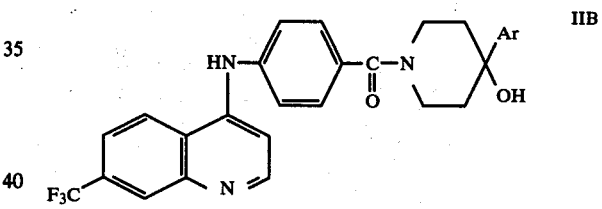

wherein Ar is phenyl substituted by one or two halo, alkyl, alkoxy, or trifluoromethyl groups, in which halo is chloro or fluoro and alkyl and alkoxy are of 1 to 3 carbon atoms, inclusive, or the pharmacologically acceptable salts thereof.

The following patents are considered related to the present invention: U.S. Pat. Nos. 3,875,165; 3,632,761; 4,025,629; and, Great Britain Pat. No. 1,443,602.

The compounds of this present invention are distinguished from the art by having substituents other than alkyl, amino and substituted amino on the D-ring. The compounds of this invention are the first to disclose substitution of aryl and/or aryl plus hydroxy groups on the heterocyclic ring D in arylaminoquinoline compounds useful as antihypertensives.

The compounds were tested for hypotensive activity and for cataractogenic activity.

The hypotensive activity of the new compounds was determined by measuring the mean arterial blood pressure at different dosage levels in the rat and determining from it the mean blood pressure reduction after 4 and 24 hours.

The mean arterial blood pressure is defined in the art as:

$$\frac{\text{systolic pressure} - \text{diastolic pressure}}{3} + \text{diastolic pressure}$$

Also, decrease of the heart rate at 4 and 24 hours after drug administration was determined.

The following is a brief description of the procedures and the basis of determining compounds to be active hypotensive agents in the assay.

Methods

Chronic abdominal aortic indwelling cannulae are exteriorized at the nape of the neck of Upjohn Sprague Dawley specific pathogen free female rats. Aortic blood pressure is monitored with a transducer-polygraph system. Mean arterial blood pressure is obtained by electrical integration of the phasic pressure. Heart rate is obtained by electronically counting arterial pulses. Two unanesthetized rats are each treated orally with single 50 mg/kg doses of the test compound. Test agents are suspended in Upjohn Vehicle 98 [each cc of water contains carboxymethylcellulose (10 mg), polysorbate 80 (4 mg) and polyparaben (0.42 mg)] or an appropriate carrier. Injection volume is 10 cc/kg. Mean arterial blood pressure and heart rate are observed before, and 4 and 24 hours after drug administration.

Results

Blood pressures of the 2 rats is averaged before and 4 and 24 hours after oral treatment with the test compound. If the change, initial vs 4 and/or 24 hours, is <5 mm Hg, the compound is considered inactive. Average change is then calculated for the group of 2 rats. If the decrease is >5 mm Hg, the compound is considered to be an active hypotensive agent.

Heart rates are also obtained before and 4 and 24 hours after drug administration. If the average change, initial vs 4 and/or 24 hours, is <65 beats per minute, the compound is not considered to have altered the heart rate. If the average change is >65 beats per minute, the compound is considered to have altered the heart rate.

An in vitro test which was used to test for cataractogenic activity of compounds can be found in Edwards, et al, Experimental Eye Research, 10, 228 (1970), and is also described below:

MATERIALS AND METHODS:

Under sterile conditions, the commercial *Grand Island Biologicals Co. Medium* #199 containing phenol red at a concentration of 0.002% was diluted 1:10 with sterile distilled water. The diluted Medium #199 was then supplemented with foetal calf serum (10%, v/v), 100 units/ml of penicillin, and 100 mg/ml of streptomycin. The final pH of this growth medium was adjusted with sterile 0.5 N sodium hydroxide.

Compounds to be tested were dissolved or suspended at a concentration of 15 mM in Vehicle 124 (0.25% methylcellulose in isotonic saline) containing 10% diluted Medium #199. When necessary, pH adjustments were made to maintain the pH at 7.2.

Eyes were removed from 11—13 day chick embryos in a sterile surface hood. All subsequent steps employed sterile techniques. Lenses were removed and freed of adhering humor. Each lens was then placed into a sterile 12×75 mm test tube containing the incubation medium described above. After all lenses were removed, an aliquot (10–100 μl) of Vehicle 124 containing Medium #199 with or without the test compound was added to a final volume of 300 μl. Paired lenses were incubated with different drugs. Each tube was stoppered with gauze-wrapped paper plugs and incubated at 36° C. Lenses were incubated for four hours after which the incubation medium containing the drug was removed by aspiration. Lenses were rinsed once with growth medium and that medium removed; 300 μl of fresh growth medium free of drug was added to the lens and the incubation was continued at 36° C. The pH changes in the growth media were determined semi-quantitatively by color comparison of the tube with a set of standard solutions prepared over the range of pH 4 to 8 and containing the same concentration of phenol red as in the growth medium.

| Color | Purple | Pink | Slightly Pink | Slightly Orange | Orange | Gold | Light Gold | Yellow |
|---|---|---|---|---|---|---|---|---|
| pH | 8 | 7.2–7.4 | 6.5 | 6 | 5.5 | 5 | 4.5 | 4 |

Color comparisons were made after 17–19 hours, 24 hours and 48 hours. In some experiments comparisons were also made at longer intervals.

As a result of the metabolism by the lenses during incubation, principally due to lactic acid formation, a decrease of the pH and change of color of the indicator from pink to yellow is observed. The compounds of formula II were found free of cataractogenic side effects and are therefore useful antihypertensive agents, which can be administered to warm-blood animals and humans.

The pharmaceutical forms of compounds of formula II (including IIA and IIB) and salts thereof contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates, lactose, proteins, lipids, calcium phosphate, cornstarch, stearic acid, methylcellulose and the like may be used as carriers or for coating purposes. Water or oils such as coconut oil, sesame oil, safflower oil, cottonseed oil, and peanut oil, may be used for preparing solutions or suspensions of the active drug. Sweetening, coloring and flavoring agents may be added.

For animals, food premixes with starch, oatmeal, dried fishmeat, fishmeal, flour, and the like, can be prepared.

This invention relates also to pharmaceutical dosage unit forms for systemic administration (oral and parenteral administration) in obtaining unexpectedly advantageous beneficial results in hypertensive conditions in mammals (including humans) and valuable warm-blooded animals such as dogs, cats, and other domestic animals. The term "dosage unit form" as used in this specification and in the claims refers to physically discrete units suitable as unitary dosages for mammalian subjects, each unit containing a predetermined quantity of the essential active ingredient calculated to produce the desired effect in combination with the required pharmaceutical means which adapt the said ingredient for systemic administration. The specification for the novel dosage unit forms of this invention are dictated by and directly dependent on the unique characteristics of the essential active ingredient and the particular effect to be achieved in view of the limitations inherent in the art of compounding such as essential active material for beneficial effects in humans and animals as disclosed in detail in this specification under preferred embodiments, these being features of the present invention. Examples of suitable dosage unit forms in accordance with this invention are tablets, capsules, orally administered liquid preparations in suitable liquid vehicles, sterile preparations in suitable liquid vehicles for intramuscular and intravenous administration, suppositories, and sterile dry preparations for the extemporaneous preparation of sterile injectable preparations in a suitable liquid vehicle. Suitable solid diluents or carriers for the solid oral pharmaceutical dosage unit forms are selected from the group consisting of lipids, carbohydrates, proteins and mineral solids, for example, starch, sucrose, kaolin, dicalcium phosphate, gelatin, acacia, corn starch, talc and the like. Capsules both hard and soft are formulated with suitable diluents and excipients, for example, edible oils, talc, calcium carbonate and the like, and also calcium stearate. Liquid preparations for oral administration are prepared in water or aqueous solutions which advantageously contain suspending agents, for example, sodium carboxymethylcellulose, methylcellulose, acacia, polyvinyl pyrrolidone, polyvinyl alcohol and the like. In the case of injectable forms, they must be sterile and must be fluid to the extent that easy syringeability exists. Such preparations must be stable under the conditions of manufacture and storage, and ordinarily contain, in addition to the basic solvent or suspending liquid, preservatives in the nature of bactericidal and fungicidal agents, for example, parabens, chlorobutanol, benzyl alcohol, phenol, and the like. In many cases it is preferable to include isotonic agents, for example, sugars or sodium chloride. Carriers and vehicles include vegetable oils, ethanol, polyols, for example, glycerol, propylene glycol, liquid polyethylene glycol and the like. Any solid preparations for subsequent extemporaneous preparation of sterile injectable preparations are sterilized, preferably by exposure to a sterilizing gas, for example, ethylene oxide. The aforesaid carriers, vehicles, diluents, excipients, preservatives, isotonic agents and the like constitute the pharmaceutical means which adapt the preparations for systemic administration.

The pharmaceutical dosage unit forms are prepared in accordance with the preceding general description to provide from about 5 to about 100 mg of the essential active ingredient per dosage unit form, which, as aforesaid, may be in the form of a solid oral preparation, a liquid oral preparation, an injectable preparation including liquid preparations and solid dry preparations for extemporaneous reconstitution to a liquid injectable preparation. The amount of the essential active ingredient provided in the pharmaceutical dosage unit forms is that amount sufficient to obtain antihypertensive effects within the effective nontoxic range. Expressed otherwise, an amount of the essential active ingredient is provided to a recipient within a range from about 0.05 mg per kg to about 20 mg per kg of body weight of the recipient, preferably 0.1 to 10 mg per kg; the most preferred dose range is 0.2 to 5 mg per kg.

The amount administered depends on the age, weight, and condition of the patient as determined by the physician.

In carrying out the process of this invention, the known starting material, 4-[[7-(trifluoromethyl or chloro)-4-quinolinyl]benzoic acid is refluxed for 3 to 6 hours with thionyl chloride. After removing the excess of thionyl chloride, the resultant acid chloride is reacted with the selected tetrahydropyridine or piperidine in pyridine or other base at room temperature (20°–25° C.). The organic phase is dried and concentrated and the resulting crystals are recrystallized from organic solvents, e.g., methanol, methylene chloride, chloroform, ethyl acetate, hexanes, mixtures thereof, and the like, to give the desired compounds II. An alternate reaction method which is used employs carbonyl diimidazole as an activating reagent to give the imidazolide which is then reacted with the appropriate amine at room temperature.

Starting 4-hydroxy-4-arylpiperidines or 4-arylpiperidines or 4-aryl-1,2,5,6-tetrahydropyridines when not commercially available can be prepared by Grignard reaction of arylmagnesium halide with 1-benzyl-4-piperidone followed by hydrolysis to give 4-hydroxy-4-aryl-1-benzylpiperidine. Catalytic hydrogenolysis removes the 1-benzyl function to give 4-hydroxy-4-arylpiperidine. This compound can be dehydrated under acidic conditions to give a 4-aryl-1,2,5,6-tetrahydropyridine which can then be reduced to give 4-arylpiperidine. These piperidines and 1,2,5,6-tetrahydropyridines are used in the following examples which are illustrative of the processes and products of the present invention, but are not to be construed as limiting.

EXAMPLE 1

4-(4-chlorophenyl)-1,2,5,6-tetrahydro-1-[4-[[7-(trifluoromethyl)-4-quinolinyl]amino]benzoyl]-pyridine A solution of 3.9 g of 4-[[7-(trifluoromethyl)-4-quinolinyl]amino]benzoic acid and thionyl chloride is allowed to reflux for 4½ hours. After isolation, the acid chloride is dissolved in 100 ml pyridine and 4.0 g of 4-[4-chlorophenyl]-1,2,5,6-tetrahydropyridine is added. The reaction is stirred overnight and then partitioned between chloroform and aqueous sodium carbonate. The organic phase is dried and concentrated. The residue is crystallized from methylene chloride. The crystals are filtered, washed with ether, and dried to yield 2.99 g (57%) of 4-(4-chlorophenyl)-1,2,5,6-tetrahydro-1-[4-[[7-(trifluoromethyl)-4-quinolinyl]-amino]benzoyl]-pyridine, of melting point 225°–226° C.

Anal. Calcd. for $C_{28}H_{21}N_3ClF_3O$ Calcd. C, 66.20; H, 4.17; H, 8.27 Found C, 66.23; H, 4.08; N, 8.29

EXAMPLE 2

4-[3-(trifluoromethyl)phenyl]-4-hydroxy-1-[4-[[7-(trifluoromethyl)-4-quinolinyl]amino]benzoyl]piperidine.

A solution of 1.0 mmol of 4-[[7-(trifluoromethyl)-4-quinolinyl]amino]benzoic acid hydrochloride in dry dimethylformamide is stirred in a nitrogen atmosphere at 20°–25° C.; 1.1 mmol of carbonyl diimidazole is added and the mixture stirred further for 1 hour. 4-Hydroxy-4-[(3-trifluoromethyl)phenyl]piperidine (1.1 mmol) is then added and the reaction mixture is stirred for 20 hours, then poured into aqueous sodium bicarbonate and is extracted with methylene chloride. The organic extract is dried over anhydrous sodium sulfate and concentrated in vacuo. The concentrate is crystallized and recrystallized from methylene chloride to give 86% yield of 4-[3-(trifluoromethyl)phenyl]-4-hydroxy-1-[4-[[7-(trifluoromethyl)-4-quinolinyl]amino]benzoyl]-piperidine of m.p. 278°–279° C.

Calcd. for $C_{29}H_{23}N_3F_6O_2$ Calcd. C, 62.25; H, 4.14; N, 7.51 Found C, 61.75; H, 4.43; N, 7.28

EXAMPLE 3

4-phenyl-1,2,5,6-tetrahydro-1-[4-[[7-(trifluoromethyl)-4-quinolinyl]amino]benzoyl]pyridine In the manner given in Example 2, 4-[[7-(trifluoromethyl)-4-quinolinyl]amino]benzoic acid is treated with carbonyl diimazole and the resulting imidazolide with 4-phenyl-1,2,5,6-tetrahydropyridine to give 4-phenyl-1,2,5,6-tetrahydro-1-[4-[[7-(trifluoromethyl)-4-quinolinyl]amino]benzoyl]pyridine of melting point 239°–241° C.

Anal. Calcd. for $C_{28}H_{22}N_3F_3O$ Calcd. C, 71.02; H, 4.68; N, 8.87 Found C, 70.20; H, 4.68; N, 8.87

EXAMPLE 4

4-[3-(trifluoromethyl)phenyl]-1,2,5,6-tetrahydro-1-[4-[[7-(trifluoromethyl)-4-quinolinyl]amino]benzoyl]pyridine In the manner given in Example 2, 4-[[7-(trifluoromethyl)-4-quinolinyl]amino]benzoic acid is treated with carbonyl diimazole and the resulting imidazolide with 4-[3-(trifluoromethyl)phenyl]-1,2,5,6-tetrahydropyridine to give 4-[3-(trifluoromethyl)phenyl]-1,2,5,6-tetrahydro-1-[4-[[7-(trifluoromethyl)-4-quinolinyl]amino]benzoyl]pyridine of melting point 220°–221° C.

Anal. Calcd. for $C_{29}H_{21}N_3F_6O$ Calcd. C, 64.32; H, 3.91; N, 7.76 Found C, 63.96; H, 4.05; N, 7.72

EXAMPLE 5

4-(3-methylphenyl)-1,2,5,6-tetrahydro-1-[4-[[7-(trifluoromethyl)-4-quinolinyl]amino]benzoyl]pyridine.

In the manner given in Example 2, 4-[[7-(trifluoromethyl)-4-quinolinyl]amino]benzoic acid is treated with carbonyl diimazole and the resulting imidazolide with 4-(3-methylphenyl)-1,2,5,6-tetrahydropyridine to give 4-(3-methylphenyl)-1,2,5,6-tetrahydro-1-[4-[[7-(trifluoromethyl)-4-quinolinyl]-amino]benzoyl]pyridine of melting point 233°–234° C.

Anal. calcd. for $C_{29}H_{24}N_3F_3O$ Calcd. C, 71.44; H, 4.96; N, 8.62 Found C, 71.30; H, 5.06; H, 8.48

EXAMPLE 6

4-phenyl-1-[4-[[7-(trifluoromethyl)-4-quinolinyl]amino]benzoyl]piperidine

In the manner given in Example 2, 4-[(7-trifluoromethyl)-4-quinolinyl]amino]benzoic acid is treated with carbonyl diimazole and the resulting imidazolide with 4-phenylpiperidine to give 4-phenyl-1-[4-[[7-(trifluoromethyl)-4-quinolinyl]amino]-benzoyl]piperidine of melting point 232°–235° C.

Anal. Calcd. for $C_{28}H_{24}N_3F_3O$ Calcd. C, 70.72; H, 5.05; N, 8.84 Found C, 70.36; H, 5.06; N, 8.87

EXAMPLE 7

4-(4-chlorophenyl)-4-hydroxy-1-[4-[[7l-(trifluoromethyl)-4-quinolinyl]amino]benzoyl]piperidine In the manner given in Example 3, 4-[[7-(trifluoromethyl)-4-quinolinyl]amino]benzoic acid is treated with carbonyl diimazole and the resulting imidazolide with 4-chlorophenyl-4-hydroxy piperidine to give 4-(4-chlorophenyl)-4-hydroxy-1-[4-[[7-(trifluoromethyl)-4-quinolinyl]amino]benzoyl]piperidine of melting point 245°–247° C.

Anal. Calcd. for $C_{28}H_{23}N_3ClF_3O_2$ Calcd. C, 63.94; H, 4.41; N, 7.99 Found C, 63.87; H, 4.43; N, 7.87

EXAMPLE 8

4-(4-methoxyphenyl)-4-hydroxy-1-[4-[[7-(trifluoromethyl)-4-quinolinyl]amino]benzoyl]piperidine In the manner given in Example 2, 4-[[7-(trifluoromethyl)-4-quinolinyl]amino]benzoic acid is treated with carbonyl diimazole and the resulting imidazolide with (4-methoxyphenyl)-4-hydroxypiperidine to give 4-(4-methoxyphenyl)-4-hydroxy-1-[4-[[7-(trifluoromethyl)-4-quinolinyl]amino]benzoyl]piperidine of melting point 251°–252° C.

Anal. Calcd. for $C_{29}H_{26}N_3F_3O_3$ Calcd. C, 66.68; H, 5.02; N, 8.06 Found C, 66.26; H, 5.03; N, 7.90

EXAMPLE 9

4-(3-methylphenyl)-4-hydroxy-1-[4-[[7-(trifluoromethyl)-4-quinolinyl]amino]benzoyl]piperidine In the manner given in Example 2, 4-[[7-(trifluoromethyl)-4-quinolinyl]amino]benzoic acid is treated with carbonyl diimazole and the resulting imidazolide with 4-(3-methylphenyl)-4-hydroxypiperidine to give 4-(3-methylphenyl)-4-hydroxy-1-[4-[[7-(trifluoromethyl]-4-quinolinyl]amino]benzoyl]piperidine of melting point 236°–238° C.

Anal. Calcd. for $C_{29}H_{26}N_3F_3O_2$ Calcd. C, 68.90; H, 5.18; N, 8.31 Found C, 68.54; H, 5.32; N, 8.10

EXAMPLE 10

4-(3-methyl-4-chlorophenyl)-4-hydroxy-1-[4-[[7-(trifluoromethyl)-4-quinolinyl]amino]benzoyl]piperidine In the manner given in Example 2, 4-[[7-(trifluoromethyl)-4-quinolinyl]amino]benzoic acid is treated with carbonyl diimazole and the resulting imidazolide with 4-(3-methyl-4-chlorophenyl)-4-hydroxypiperidine to give 4-(3-methyl-4-chlorophenyl)-4-hydroxy-1-[4-[[7-(trifluoromethyl)-4-quinolinyl]-amino]benzoyl]piperidine.

EXAMPLE 11

4-(2-oxo-1-benzimidazolinyl)-1-[4-[[7-(trifluoromethyl)-4-quinolinyl]amino]benzoyl]piperidine In the manner given in Example 2, 4-[[7(trifluoromethyl)-4-quinolinyl]amino]benzoic acid hydrochloride is treated with carbonyl diimazole and the resultant imidsazolide with 4-(1-benzimidazolyl)-piperidine to give 4-(2-oxo-1benzimidazolinyl)-1-[4-[[7-(trifluoromethyl)-4-quinolinyl]amino]benzoyl]piperidine of melting point >300° C. IR and NMR spectra are consistent with the structure assigned to 4-(2-oxo-1-benzimidazolinyl)-1-[4-[[7-(trifluoromethyl)-4-quinolinyl]amino]benzoyl]piperidine.

EXAMPLE 12

4-(4-methoxyphenyl)-1,2,5,6-tetrahydro-1-[4-[[7-(trifluoromethyl)-4-quinolinyl]amino]benzoyl]pyridine In the manner given in Example 2, 4-[[7-(trifluoromethyl)-4-quinolinyl]amino]benzoic acid is treated with carbonyl diimazole and the resulting imidazolide with 4-(4-methoxyphenyl)-1,2,5,6-tetrahydropyridine to give 4-(4-methoxyphenyl)-1,2,5,6-tetrahydro-1-[4-[[7-(trifluoromethyl)-4-quinolinyl]amino]benzoyl]pyridine of melting point 237°–238.5° C.

Anal. Calcd. for $C_{29}H_{24}N_3O_2F_3$ Calcd. C, 69.17; H, 4.80; N, 8.34 Found C, 69.04; H, 4.93; N, 8.35

EXAMPLE 13

4-(3-bromophenyl)-4-hydroxy-1-[4-[[7-(trifluoromethyl)-4-quinolinyl]amino]benzoyl]piperidine In the manner given in Example 1, 4-[[7-(trifluoromethyl)-4-quinolinyl]amino]benzoic acid is treated with thionyl chloride, and the resulting acid chloride with 4-(3-bromophenyl)-4-hydroxypiperidine to give 4-(3-bromophenyl)-4-hydroxy-1-[4-[[7-(trifluoromethyl)-4-quinolinyl]amino]-benzoyl]piperidine.

EXAMPLE 14

4-(4-fluorophenyl)-1,2,5,6-tetrahydro-1-[4-[[7-(trifluoromethyl)-4-quinolinyl]amino]benzoyl]pyridine In the manner given in Example 1, 4-[[7-(trifluoromethyl)-4-quinolinyl]amino]benzoic acid is treated with thionyl chloride and the resulting acid chloride with 4-(4-fluorophenyl)-1,2,5,6-tetrahydropyridine to give 4-(4-fluorophenyl)-1,2,5,6-tetrahydro-1-[4-[[7-(trifluoromethyl)-4-quinolinyl]-amino]benzoyl]pyridine.

EXAMPLE 15

4-(4-fluorophenyl)-4-hydroxy-1-[4-[[7-(trifluoromethyl)-4-quinolinyl]amino]benzoyl]piperidine In the manner given in Example 2, 4-[[7-(trifluoromethyl)-4-quinolinyl]amino]benzoic acid is treated with carbonyl diimidazole and the resulting imidazolide with 4-(4-fluorophenyl)-4-hydroxypiperidine to give 4-(4-fluorophenyl)-4-hydroxy-1[4-[[7-(trifluoromethyl)-4-quinolinyl]amino]benzoyl]piperidine.

EXAMPLE 16

4-(4-bromophenyl)-1,2,5,6-tetrahydro-1[4-[[7-(trifluoromethyl)-4-quinolinyl]amino]benzoyl]-pyridine In the manner given in Example 1, 4-[[7-(trifluoromethyl)-4-quinolinyl]amino]benzoic acid is treated with thionyl chloride and the resulting acid chloride with 4-(4-bromophenyl)-1,2,5,6-tetrahydropyridine to give 4-(4-bromophenyl)-1,2,5,6-tetrahydro1-[4-[[7-(trifluoromethyl)-4-quinolinyl]-amino]benzoyl]pyridine.

EXAMPLE 17

4-(3-ethylphenyl)-4-hydroxy-1-[4-[[7-(trifluoromethyl)-4-quinolinyl]amino]benzoyl]piperidine In the manner given in Example 2, 4-[[7-(trifluoromethyl)-4-quinolinyl]amino]benzoic acid is treated with carbonyl diimidazole and the resulting imidazolide with 4-(3-ethylphenyl)-4-hydroxypiperidine to give 4-(3-ethylphenyl)-4-hydroxy-1-[4-[[7-(trifluoromethyl)-4-quinolinyl]amino]benzoyl]piperidine.

EXAMPLE 18

4-(3-ethoxyphenyl)-1,2,5,6-tetrahydro-1-[4-[[7-(trifluoromethyl)-4-quinolinyl]amino]benzoyl]-pyridine In the manner given in Example 1, 4-[[7-(trifluoromethyl)-4-quinolinyl]amino]benzoic acid is treated with thionyl chloride and the resulting acid chloride with 4-(3-ethoxyphenyl)-1,2,5,6-tetrahydropyridine to give 4-(3-ethoxyphenyl)-1,2,5,6-tetrahydro-1-[4-[[7-(trifluoromethyl)-4-quinolinyl]amino]benzoyl]pyridine.

EXAMPLE 19

4-(4-ethylphenyl)-4-hydroxy-1-[4-[[7-(trifluoromethyl)-4-quinolinyl]amino]benzoyl]piperidine In the manner given in Example 1, 4-[[7-(trifluoromethyl)-4-quinolinyl]amino]benzoic acid is treated with thionyl chloride and the resulting acid chloride with 4-(4-ethylphenyl)-4-hydroxypiperidine to give 4-(4-ethylphenyl)-4-hydroxy-1-[4-[[7-(trifluoromethyl)-4-quinolinyl]amino]benzoyl]piperidine.

EXAMPLE 20

4-(3-propylphenyl)-1,2,5,6-tetrahydro-1-[4-[[7-(trifluoromethyl)-4-quinolinyl]amino]benzoyl]pyridine In the manner given in Example 1, 4-[[7-(trifluoromethyl)-4-quinolinyl]amino]benzoic acid is treated with thionyl chloride and the resulting acid chloride with 4-(3-propylphenyl)-1,2,5,6-tetrahydropyridine to give 4-(3-propylphenyl)-1,2,5,6-tetrahydro-1-[4-[[7-(trifluoromethyl)-4-quinolinyl]amino]benzoyl]pyridine.

EXAMPLE 21

4-(3-bromophenyl)-1,2,5,6-tetrahydro-1-[4-[[7-chloro-4-quinolinyl]amino]benzoyl]pyridine In the manner given in Example 1, 4-[[7-chloro-4-quinolinyl]amino]benzoic acid is treated with thionyl chloride and the resulting acid chloride with 4-(3-bromophenyl)-1,2,5,6-tetrahydropyridine to give 4-(3-bromophenyl)-1,2,5,6-tetrahydro-1-[4-[[7-chloro-4-quinolinyl]amino]benzoyl]pyridine.

EXAMPLE 22

4-(3-propylphenyl)-4-hydroxy-1-[4-[[7-chloro-4-quinolinyl]amino]benzoyl]piperidine In the manner given in Example 2, 4-[[7-chloro-4-quinolinyl]amino]benzoic acid is treated with carbonyl diimidazole and the resulting imidazolide with 4-(3-propylphenyl)-4-hydroxypiperidine to give 4-(3-propylphenyl)-4-hydroxy-1-[4-[[7-chloro-4-quinolinyl]amino]benzoyl]piperidine.

EXAMPLE 23

4-(3-methoxyphenyl)-1,2,5,6-tetrahydro-1-[4-[[7-chloro-4-quinolinyl]amino]benzoyl]pyridine In the manner given in Example 1, 4-[[7-chloro-4-quinolinyl]amino]benzoic acid is treated with thionyl chloride and the resulting acid chloride with 4-(3-methoxyphenyl)-1,2,5,6-tetrahydropyridine to give 4-(3-methoxyphenyl)-1,2,5,6-tetrahydro-1-[4-[[7-chloro-4-quinolinyl]amino]-benzoyl]pyridine.

EXAMPLE 24

4-(4-chlorophenyl)-1,2,5,6-tetrahydro-1-[4-[[7-chloro-4-quinolinyl]amino]benzoyl]pyridine In the manner given in Example 2, 4-[[7-chloro-4-quinolinyl]amino]benzoic acid is treated with carbonyl diimidazole and the resulting imidazolide with 4-(4-chlorophenyl)-1,2,5,6-tetrahydropyridine to give 4-(4-chlorophenyl)-1,2,5,6-tetrahydro-1-[4-[[7-chloro-4-quinolinyl]amino]benzoyl]pyridine.

EXAMPLE 25

4-(4-propoxyphenyl)-1-[4-[[7-chloro-4-quinolinylamino]benzoyl]piperidine

In the manner given in Example 1, 4-[[7-chloro-4-quinolinyl]amino]benzoic acid is treated with thionyl chloride and the resulting acid chloride with 4-(4-propoxyphenyl)piperidine to give 4(4-propoxyphenyl)-1-[4-[[7-chloro-4-quinolinyl]amino]-benzoyl]piperidine.

EXAMPLE 26

4-(3-ethoxyphenyl)-1,2,5,6-tetrahydro-1-[4-[[7-chloro-4-quinolinyl]amino]benzoyl]pyridine In the manner given in Example 2, 4-[[7-chloro-4-quinolinyl]amino]benzoic acid is treated with carbonyl diimidazole and the resulting imidazolide with 4-(3-ethoxypyridine)-1,2,5,6-tetrahydropyridine to give 4-(3- ethoxyphenyl)-1,2,5,6-tetrahydro-1-[4-[[7-chloro-4-quinolinyl]amino]benzoyl]pyridine.

EXAMPLE 27

4-(3-chlorophenyl)-4-hydroxy-1-[4-[[7-chloro-4-quinolinyl]amino]benzoyl]piperidine In the manner given in Example 2, 4-[[7-chloro-4-quinolinyl]amino]benzoic acid is treated with carbonyl diimidazole and the resulting imidazolide with 4-(3-chlorophenyl)-4-hydroxypiperidine to give 4-(3-chlorophenyl)-4-hydroxy-1-[4-[[7-chloro-4-quinolinyl]amino]benzoyl]piperidine.

EXAMPLE 28

4-(4-fluorophenyl)-1,2,5,6-tetrahydro-1-[4-[[7-chloro-4-quinolinyl]amino]benzoyl]pyridine In the manner given in Example 1, 4-[[7-chloro-4-quinolinyl]amino]benzoic acid is treated with thionyl chloride and the resulting acid chloride with 4-(4-fluorophenyl)-1,2,5,6-tetrahydropyridine to give 4-(4-fluorophenyl)-1,2,5,6-tetrahydro-1-[4-[[7-chloro-4-quinolinyl]amino]benzoyl]pyridine.

EXAMPLE 29

4-[3-(trifluoromethyl)phenyl]-1,2,5,6-tetrahydro-1-[4-[[7-chloro-4-quinolinyl]amino]benzoyl]-pyridine In the manner given in Example 1, 4-[[7-chloro-4-quinolinyl]amino]benzoic acid is treated with thionyl chloride and the resulting acid chloride with 4-[3-(trifluoromethyl)phenyl]-1,2,5,6-tetrahydropyridine to give 4-[3-(trifluoromethyl)phenyl]-1,2,5,6-tetrahydro-1-[4-[[7-chloro-4-quinolinyl]-amino]benzoyl]pyridine.

EXAMPLE 30

4-[4-(trifluoromethyl)phenyl]-4-hydroxy-1-[4-[[7-chloro-4-quinolinyl]amino]benzoyl]piperidine In the manner given in Example 1, 4-[[7-chloro-4-quinolinyl]amino]benzoic acid is treated with thionyl chloride and the resulting acid chloride with 4-hydroxy-[4-(trifluoromethyl)phenyl]piperidine to give 4-[4-(trifluoromethyl)phenyl]-4-hydroxy-1-[4-[[7-chloro-4-quinolinyl]amino]benzoyl]-piperidine.

EXAMPLE 31

4-(4-ethoxyphenyl)-4-hydroxy-1-[4-[[7-chloro-4-quinolinyl]amino]benzoyl]piperidine In the manner given in Example 2, 4-[[7-chloro-4-quinolinyl]amino]benzoic acid is treated with carbonyl diimidazole and the resulting imidazolide with 4-(4-ethoxyphenyl)-4-hydroxypiperidine to give 4-(4-ethoxyphenyl)-4-hydroxy-1-[4-[[7-chloro-4-quinolinyl]amino]benzoyl]piperidine.

EXAMPLE 32

4-[4-(trifluoromethyl)phenyl]-4-hydroxy-1-[4-[[7-trifluoromethyl-4-quinolinyl]amino]benzoyl]-piperidine Ia the manner given in Example 2, 4-[[7-trifluoromethyl-4-quinolinyl]amino]benzoic acid hydrochloride is treated with carbonyl diimidazole and the resultant imidazolide with 4-(3-trifluoromethyl)-phenyl-4-hydroxypiperidine to give 2.10 g of 4-hydroxy-4-(3-trifluoromethyl)phenyl-1-[4-[[7-trifluoromethyl-4-quinolinyl]amino]benzoyl]piperidine which is crystallized from ethanol, melting point 269°-271° C.

Anal. Calcd. for $C_{29}H_{23}N_3F_6O_2$ Calcd. C, 62.25; H, 4.14; N, 7.51 Found C, 61.80; H, 4.32; N, 7.71

EXAMPLE 33

Using either of the procedures found in Examples 1 and 2, the following illustrative compounds are prepared starting from the 4-[[7-chloro- or trifluoromethyl-4-quinolinyl]amino]benzoic acid and the appropriate 1,2,5,6-tetrahydropyridine.

4-(3,4-dichlorophenyl)-1,2,5,6-tetrahydro-1-[4-[[7-trifluoromethyl-4-quinolinyl]amino]benzoyl]-pyridine 4-(3,4-dimethoxyphenyl)-1,2,5,6-tetrahydro-1-[4-[[7-trifluoromethyl-4-quinolinyl]amino]benzoyl]-pyridine 4-(3-chloro-5-ethylphenyl)-1,2,5,6-tetrahydro-1-[4-[[7-trifluoromethyl-4-quinolinyl]amino]benzoyo]-pyridine 4-(2,4-diethoxyphenyl)-1,2,5,6-tetrahydro-1-[4-[[7-trifluoromethyl-4-quinolinyl]amino]benzoyl]-pyridine 4-(3-fluoro-4-methoxyphenyl)-1,2,5,6-tetrahydro-1-[4-[[7-trifluoromethyl-4-quinolinyl]amino]benzoyl]pyridine 4-(3,4-dibromophenyl)-1,2,5,6-tetrahydro-1-[4-[[7-chloro-4-quinolinyl]amino]benzoyl]pyridine 4-(3-ethyl-4-trifluoromethylphenyl)-1,2,5,6-tetrahydro-1-[4-[[7-chloro-4-quinolinyl]amino]benzoyl]-pyridine 4-(2,4-difluorophenyl)-1,2,5,6-tetrahydro-1-[4-[[7-chloro-4-quinolinyl]amino]benzoyl]pyridine

EXAMPLE 34

Using either of the procedures found in Examples 1 and 2, the following illustrative compounds are prepared starting from the 4-[[7-chloro- or trifluoromethyl-4-quinolinyl]-amino]benzoic acid and the appropriate piperidine.

4-(3,4-dichlorophenyl)-4-hydroxy-1-[4-[[7-trifluoromethyl-4-quinolinyl]amino]benzoyl]piperidine 4-(3-fluoro-4-trifluoromethylphenyl)-4-hydroxy-1-[4-[[7-trifluoromethyl-4-quinolinyl]amino]benzoyl]-piperidine 4-(2,4-diethylphenyl)-4-hydroxy-1-[4-[[7-trifluoromethyl-4-quinolinyl]amino]benzoyl]piperidine 4-(3-ethoxyphenyl)-4-hydroxy-1-[4-[[7-trifluoromethyl-4-quinolinyl]amino]benzoyl]piperidine 4-(4-propylphenyl)-4-hydroxy-1-[4-[[7-trifluoromethyl-4-quinolinyl]amino]benzoyl]piperidine 4-(3,4-dibromophenyl)-4-hydroxy-1-[4-[[7-trifluoromethyl-4-quinolinyl]amino]benzoyl]piperidine 4-(3,4-dimethoxyphenyl)-4-hydroxy-1-[4-[[7-chloro-4-quinolinyl]amino]benzoyl]piperidine 4-(2,3-dichlorophenyl)-4-hydroxy-1-[4-[[7-chloro-4-quinolinyl]amino]benzoyl]piperidine 4-(2-methoxy-4-trifluoromethylphenyl)-4-hydroxy-1-[4-[[7-chloro-4-quinolinyl]amino]benzoyl]piperidine 4-(3-trifluoromethylphenyl)-4-hydroxy-1-[4-[[7-chloro-4-quinolinyl]amino]benzoyl]piperidine 4-(3,4-difluorophenyl)-1-[4-[[7-trifluoromethyl-4-quinolinyl]amino]benzoyl]piperidine 4-(4-trifluoromethylphenyl)-1-[4-[[7-trifluoromethyl-4-quinolinyl]amino]benzoyl]piperidine 4-(3-methyl-4-chlorophenyl)-1-[4-[[7-trifluoromethyl-4-quinolinyl]amino]benzoyl]piperidine 4-(4-trifluoromethylphenyl)-1-[4-[[7-chloro-4-quinolinyl]amino]benzoyl]piperidine 4-(3,4-diethylphenyl)-1-[4-[[7-chloro-4-quinolinyl-]amino]benzoyl]piperidine The pharmacologically acceptable acid addition salts of compounds of formula II (as well as of formula IIA and IIB) can be prepared and isolated by conventional processes, such as reacting a compound of formula II with a selected pharmacologically acceptable acid. Such acids include hydrochloric, hybrobromic, phosphoric, sulfuric, acetic, tartaric, lactic, citric, malic, maleic, methanesulfonic, pamoic, benzenesulfonic, cyclohexanesulfamic acids, toluenesulfonic, and the like. The reaction is conveniently performed in an organic solvent, e.g., ether, dioxane or tetrahydrofuran, ethanol, methanol, ethyl acetate; the salts can be recovered by crystallization, precipitation or evaporating the solvent. These salts are useful in the same manner as the free base.

The compounds of formulae II, IIA, and IIB, or their acid addition salts in their crystalline state, can be isolated as solvates, e.g., with a discrete quantity of solvent, such as water, ethanol, and the like, associated physically, and thus removable without effective alteration of the chemical entity per se.

This invention is not intended to be limited to any one particular stereoisomeric form.

The following examples set forth illustrative formulations which are useful for the practice of this invention:

EXAMPLE 35

One thousand tablets for oral use, each containing 50 mg of 4-phenyl-1,2,5,6-tetrahydro-1-[4-[[7-(trifluoromethyl)-4-quinolinyl]amino]benzoyl]pyridine as essential active ingredient are prepared from the following ingredients:

| Essential active ingredient | 50 | g |
|---|---|---|
| Dicalcium phosphate | 150 | g |
| Methylcellulose, U.S.P. (15 cps) | 6.5 | g |
| Talc | 20 | g |
| Calcium stearate | 2.5 | g |

The essential active ingredient and dicalcium phosphate are mixed well, granulated with 7.5% aqueous solution of methylcellulose, passed through a No. 8 screen and dried carefully. The dried granules are passed through a No. 12 screen, mixed with the talc and stearate and compressed into tablets. These tablets are useful in the treatment of severe hypertension in adult humans at a dose of 1 tablet 2 or 3 times a day.

EXAMPLE 36

One thousand two-piece hard gelatin capsules for oral use, each capsule containing 75 mg of 4-phenyl-1-[4-[[7-(trifluoromethyl)-4-quinolinyl]amino]benzoyl]-piperidine as essential active ingredient are prepared from the following ingredients:

| Essential active ingredient | 75 g |
|---|---|
| Lactose, U.S.P. | 100 g |
| Starch, U.S.P. | 10 g |
| Talc, U.S.P. | 5 g |
| Calcium stearate | 1 g |

The finely powdered materials are mixed thoroughly, then filled into hard gelatin capsules of appropriate size.

A satisfactory clinical response is obtained in adults showing hypertension with 1 capsule 4 times a day.

EXAMPLE 37

One-piece soft elastic capsules for oral use, each containing 10 mg of 4-(3-trifluoromethylphenyl)-4-hydroxy-1-[4-[[7-(trifluoromethyl)-4-quinolinyl]-amino]benzoyl]piperidine as essential active ingredient are prepared in the usual manner by first dispersing the powdered active material in sufficient corn oil to render the material capsulatable.

EXAMPLE 38

An aqueous oral preparation containing in each teaspoonful (5 ml) 15 mg of 4-hydroxy-4-(4-trifluoromethyl)phenyl-1-[4-[[7-(trifluoromethyl)-4-quinolinyl]amino]benzoyl]piperidine as essential active ingredient is prepared from the following ingredients:

| Essential active ingredient hydrochloride | 20 g |
|---|---|
| Methylparaben, U.S.P. | 7.5 g |
| Propylparaben, U.S.P. | 2.5 g |
| Saccharin sodium | 12.5 g |
| Cyclamate sodium | 2.5 g |
| Glycerin | 3000 ml |
| Tragacanth powder | 10 g |
| Orange oil flavor | 10 g |
| F.D. and C. Orange dye | 7.5 g |
| Deionized water, Q.S. to | 10,000 ml |

The foregoing aqueous preparation is useful in the treatment of adult hypertension at a dose of 1 teaspoonful 4 times a day.

EXAMPLE 39

A sterile aqueous suspension suitable for intramuscular injection and containing in each milliliter, 2 mg of 4-hydroxy-4-(4-trifluoromethyl)phenyl-1-[4-[[7-(trifluoromethyl)-4-quinolinyl]amino]benzoyl]-piperidine as essential active ingredient is prepared from the following ingredients:

| Essential active ingredient | 2 g |
|---|---|
| Polyethylene glycol 4000, U.S.P. | 3 g |
| Sodium chloride | 0.9 g |
| Polysorbate 80, U.S.P. | 0.4 g |
| Sodium metabisulfite | 0.1 g |
| Methylparaben, U.S.P. | 0.18 g |
| Propylparaben, U.S.P. | 0.02 g |
| Water for injection, q.s. to | 1000 ml |

The preceding sterile injectable is useful in the treatment of moderate hypertension at a dose of 1 or 2 ml.

EXAMPLE 40

One thousand suppositories, each weighing 2.5 g and containing 100 mg of 4-hydroxy-4-(3-trifluoromethyl)-phenyl-1-[4-[[7-(trifluoromethyl)-4-quinolinyl]amino]-benzoyl]piperidine as essential active ingredient are prepared from the following ingredients:

| Essential active ingredient | 100 g |
|---|---|
| Propylene glycol | 165 g |
| Polyethylene glycol 4000 q.s. | 2500 g |

The essential active ingredient is added to the propylene glycol and the mixture milled until uniformly dispersed. The PEG 4000 is melted and the propylene glycol dispersion added. The suspension is poured into molds and allowed to cool and solidify.

These suppositories are useful in the treatment of moderate hypertension in adult humans at a dose of 1 suppository rectally three times a day.

EXAMPLE 41

One thousand hard gelatin capsules for oral use, each containing 10 mg of 4-hydroxy-4-(4-chlorophenyl)-1-[4-[[7-(trifluoromethyl)-4-quinolinyl]amino]benzoyl]-piperidine as essential active ingredient and 25 mg of hydrochlorothiazide are prepared from the following ingredients:

| Essential active ingredient, micronized | |
|---|---|
| Hydrochlorothiazide | 25 g |
| Starch | 125 g |
| Talc | 25 g |

One capsule 4 times a day is useful in the relief of moderate hypertension in adult humans.

EXAMPLE 42

Ten thousand scored tablets for oral use, each containing 25 mg of 4-hydroxy-4-(3-trifluoromethyl)-phenyl-1-[4-[[7-(trifluoromethyl)-4-quinolinyl]-amino]benzoyl]piperidine as essential active ingredient and 0.08 mg of reserpine, are prepared from the following ingredients and using the procedure of

EXAMPLE 35

| Essential active ingredient, micronized | 250 | g |
|---|---|---|
| Reserpine | 0.8 | g |
| Lactose | 1500 | g |
| Corn starch | 500 | g |
| Talc | 500 | g |
| Calcium stearate | 25 | g |

This combination of active materials is effective in reducing hypertension in adult humans. The dose is one-half to two tablets 3 times a day depending on the severity of the condition.

EXAMPLE 43

Ten thousand tablets for oral use, each containing 60 mg of 4-(3-trifluoromethyl)-1,2,5,6-tetrahydro-1-[4-[[7-(trifluoromethyl)-4-quinolinyl]amino]-benzoyl]piperidine as the essential active ingredient and 320 mg acetaminophen are prepared from the following ingredients and using the procedure of Example 35.

| Essential active ingredient, micronized | 600 g |
|---|---|
| Acetaminophen, filely powdered | 3200 g |
| Lactose | 1000 g |
| Corn Starch | 500 g |
| Talc | 500 g |
| Calcium stearate | 25 g |

This tablet is useful in treating adult humans suffering from hypertension by administering 1 tablet 3 times a day, depending on the severity of the condition.

Following the procedure of the preceding Examples 35–43 but substituting appropriate dosages of the following representative compounds as essential active ingredients, useful formulations are made:

4-(3-methylphenyl)-1,2,5,6-tetrahydro-1-[4-[[7-trifluoromethyl-4-quinolinyl]amino]benzoyl]pyridine 4-(4-chlorophenyl)-1-[4-[[7-trifluoromethyl-4-quinolinyl]amino]benzoyl]piperidine 4-(4-methoxyphenyl)-4-hydroxy-1-[4-[[7-trifluoromethyl-4-quinolinyl]amino]benzoyl]piperidine 4-(3-methylphenyl)-4-hydroxy-1-[4-[[7-trifluoromethyl-4-quinolinyl]amino]benzoyl]piperidine 4-(4-fluorophenyl)-1,2,5,6-tetrahydro-1-[4-[[7-trifluoromethyl-4-quinolinyl]amino]benzoyl]-pyridine 4-(3-methylphenyl)-1,2,5,6-tetrahydro-1-[4-[[7-chloro-4-quinolinyl]amino]benzoyl]pyridine Although not necessary in the embodiment of the inventive concept, additional active ingredients are incorporated in the present pharmaceutical dosage unit forms as desired. Each pharmaceutical dosage unit form contains therein an amount within the following non-toxic effective ranges: antihypertensive and diuretic agents such as reserpine (0.05 to 1 mg), hydralazine (10 to 100 mg), methyldopa (100 to 250 mg), guanethidine (10 to 50 mg), hydrochlorothiazide (15 to 50 mg), and ethoxzolamide (50 to 150 mg); tranquilizers, antipsychotic and anti-anxiety agents such as chlorpromazine (5 to 50 mg), thioridazine (5 to 100 mg), haloperidol (0.5 to 5 mg), meprobamate (100 to 400 mg), chlordiazepoxide (5 to 50 mg), diazepam (2 to 15 mg), and ectylurea (100 to 300 mg); barbiturates such as phenobarbitol (8 to 60 mg), butabarbitol (8 to 60 mg), and amobarbitol (16 to 120 mg); analgesics such as aspirin (150 to 500 mg) and acetaminophen (150 to 600 mg); or antidepressants such as amitriptyline hydrochloride (10 to 50 mg), methylphenidate hydrochloride (5 to 20 mg), d-amphetamine sulfate (2 to 15 mg), methamphetamine hydrochloride (2 to 15 mg), and melitracen (15 to 50 mg).

What is claimed is:

1. A compound of the formula

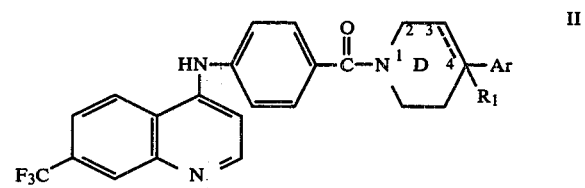

wherein D is a piperidino or 1,2,5,6-tetrahydropyridino ring;

wherein $R_1$ is hydrogen or hydroxy when the D is piperidino, or absent when the D is 1,2,5,6-tetrahydropyridino; and wherein Ar is 2-oxo-1-benzimidazolinyl, phenyl, or phenyl substituted by one or two halo, trifluoromethyl, alkyl of one to 3 carbon atoms, inclusive, or alkoxy of one to 3 carbon atoms, inclusive, and halo is chloro, bromo, or fluoro; or the pharmacologically acceptable acid addition salts thereof.

2. A compound according to claim 1 of the formula IIA

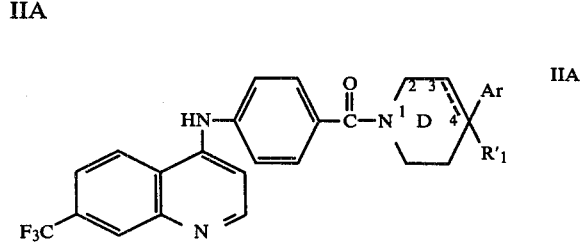

wherein the D is piperidino, $R'_1$ is hydroxy; and Ar is phenyl substituted by one or two halo, alkyl, alkoxy or trifluoromethyl in which halo is chloro or fluoro; or wherein D is 1,2,5,6-tetrahydropyridino, R'₁ is absent and Ar is phenyl or phenyl substituted with one or two halo, alkyl, alkoxy, or trifluoromethyl groups, wherein halo, alkyl and alkoxy are as defined above; or the pharmacologically acceptable acid addition salts thereof.

3. A compound according to claim 1 of the formula IIB

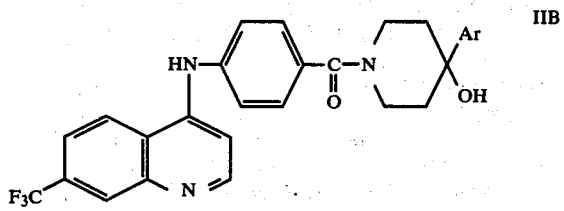

wherein Ar is phenyl substituted by one or two halo, alkyl, alkoxy, or trifluoromethyl groups in which halo is chloro or fluoro and alkyl and alkoxy are from 1 to 3 carbon atoms; or the pharmacologically acceptable acid addition salts thereof.

4. A compound according to claim 1 wherein D is piperidino, R₁ is hydrogen, Ar is phenyl and the compound is therefore 4-phenyl-1-[4-[[7-(trifluoromethyl)-4-quinolinyl]-amino]benzoyl]piperidine.

5. A compound according to claim 2 wherein D is piperidino, R'₁ is hydrogen, Ar is 4-chlorophenyl and the compound is therefore 4-(4-chlorophenyl(-4-hydroxy-1-[4-[[7-(trifluoromethyl)-4-quinolinyl]amino]-benzoyl]piperidine.

6. A compound according to claim 3 wherein Ar is 4-methoxyphenyl and the compound is therefore 4-(4-methoxyphenyl)-4-hydroxy-1-[4-[[7-(trifluoromethyl)-4-quinolinyl]amino]benzoyl]piperidine.

7. A compound according to claim 2 wherein D is piperidino, R'₁ is hydroxy, Ar is 3-methylphenyl and the compound is therefore 4-(3-methylphenyl)-4-hydroxy-[4-[[7-(trifluoromethyl)-4-quinolinyl]amino]benzoyl]-piperidine.

8. A compound according to claim 3 wherein Ar is 3-trifluoromethylphenyl and the compound is therefore 4-[3-(trifluoromethyl(phenyl]-4-hydroxy-1-[4-[[7-(trifluoromethyl(-4-quinolinyl]amino]benzoyl]piperidine.

9. A compound according to claim 2 wherein D is 1,2,5,6-tetrahydropyridino, Ar is 3-methylphenyl and the compound is therefore 4-(3-methylphenyl)-1,2,5,6-tetrahydro-1-[4-[[7-(trifluoromethyl)-4-quinolinyl-]amino]-benzoyl]pyridine.

10. A compound according to claim 2 wherein D is 1,2,5,6-tetrahydropyridine, Ar is 4-chlorophenyl and the compound is therefore 4-(4-chlorophenyl)-1,2,5,6-tetrahydro-1[4-[[7-(trifluoromethyl)-4-quinolinyl-]amino]-benzoyl]pyridine.

11. A compound according to claim 2 wherein D is 1,2,5,6-tetrahydropyridine, Ar is phenyl and the compound is therefore 4-phenyl-1,2,5,6-tetrahydro-1[4-[[7-(trifluoromethyl)-4-quinolinyl]amino]benzoyl]pyridine.

12. A compound according to claim 2 wherein D is 1,2,5,6-tetrahydropyridine, Ar is 3-(trifluoromethyl)-phenyl and the compound is therefore 4-[3-(trifluoromethyl)phenyl]-1,2,5,6-tetrahydro-1[4-[[7-(trifluoromethyl)-4-quinolinyl]amino]benzoyl]pyridine.

13. A compound according to claim 3 wherein Ar is 4-trifluoromethylphenyl and the compound is therefore 4-(4-trifluoromethylphenyl)-4-hydroxy-1-[4-[[7-(trifluoromethyl)-4-quinolinyl]amino]benzoyl]piperidine.

14. A compound according to claim 2 wherein D is 1,2,5,6-tetrahydropyridine, Ar is 4-methoxyphenyl and the compound is therefore 4-(4-methoxyphenyl)-1,2,5,6-tetrahydro-1-[4-[[7-(trifluoromethyl)-4-quinolinyl]-amino]benzoyl]pyridine.

15. A pharmaceutical formulation for systemic administration to alleviate hypertension consisting essentially of an effective non-toxic amount of a compound of the formula

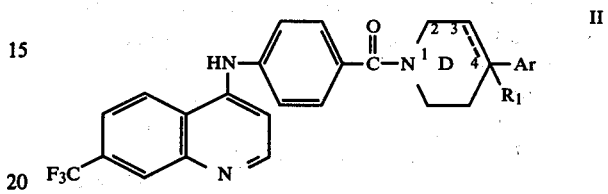

wherein D is a piperidino or 1,2,5,6-tetrahydropyridino ring;

wherein R₁ is hydrogen or hydroxy when the D is piperidino, or absent when the D is 1,2,5,6-tetrahydropyridino; and wherein Ar is 2-oxo-1-benzimidazolinyl, phenyl, or phenyl substituted by one or two halo, trifluoromethyl, alkyl of one to 3 carbon atoms, inclusive, or alkoxy of one to 3 carbon atoms, inclusive, and halo is chloro, bromo, or fluoro; or the pharmacologically acceptable acid addition salts thereof.

16. The composition according to claim 15 wherein the compound used in effective non-toxic amounts is that of formula IIA:

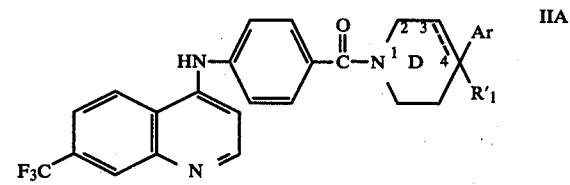

wherein the D is piperidino, R'₁ is hydroxy; and Ar is phenyl substituted by one or two halo, alkyl, alkoxy or trifluoromethyl in which halo is chloro or fluoro; or wherein D is 1,2,5,6-tetrahydropyridino, R'₁ is absent and Ar is phenyl or phenyl substituted with one or two halo, alkyl, alkoxy, or trifluoromethyl groups, wherein halo, alkyl and alkoxy are as defined above; or the pharmacologically acceptable acid addition salts thereof.

17. The composition according to claim 15 wherein the compound used in effective non-toxic amounts is that of formula IIB:

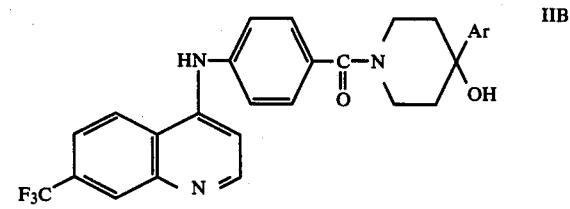

wherein Ar is phenyl substituted by one or two halo, alkyl, alkoxy, or trifluoromethyl groups in which halo is chloro or fluoro and alkyl and alkoxy are from 1 to 3 carbon atoms; or the pharmacologically acceptable acid addition salts thereof.

18. The composition according to claim 16 wherein the compound used in effective non-toxic amount is 4-(4-chlorophenyl(-1,2,5,6-tetrahydro-1-[4-[[7-(trifluoromethyl)-4-quinolinyl]amino]benzoyl]pyridine.

19. The composition according to claim 16 wherein the compound used in effective non-toxic amount is 4-(3-trifluoromethylphenyl)-1,2,5,6-tetrahydro-1-[4-[[7-(trifluoromethyl)-4-quinolinyl]amino]benzoyl]pyridine.

20. The composition according to claim 17 wherein the compound used in effective non-toxic amount is 4-hydroxy-4-(4-chlorophenyl)-1-[4-[[7-(trifluoromethyl)-4-quinolinyl]-amino]benzoyl]piperidine.

21. The composition according to claim 17 wherein the compound used in effective non-toxic amount is 4-hydroxy-4-(3-trifluoromethylphenyl)-1-[4-[[7-(trifluoromethyl)-4-quinolinyl]amino]benzoyl]piperidine.

22. The composition according to claim 17 wherein the compound used in effective non-toxic amount is 4-hydroxy-4-(4-trifluoromethylphenyl)-1-[4-[[7-(trifluoromethyl)-4-quinolinyl]amino]benzoyl]piperidine.

23. A method of obtaining antihypertensive effects in a mammal which consists essentially of administering systemically to the mammal a pharmaceutical dosage unit form supplying an effective non-toxic amount for antihypertensive effects of a compound of the formula II:

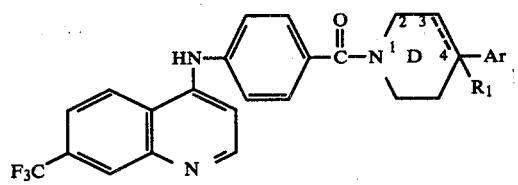

wherein D is a piperidino or 1,2,5,6-tetrahydropyridino ring;
wherein R₁ is hydrogen or hydroxy when the D is piperidino, or absent when the D is 1,2,5,6-tetrahydropyridino; and
wherein Ar is 2-oxo-1-benzimidazolinyl, phenyl, or phenyl substituted by one or two halo, trifluoromethyl, alkyl of one to 3 carbon atoms, inclusive, or alkoxy of one to 3 carbon atoms, inclusive, and halo is chloro, bromo, or fluoro; or the pharmacologically acceptable acid addition salts thereof.

24. A method according to claim 23 wherein the compound is of the formula IIA:

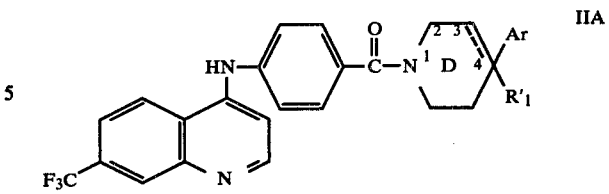

wherein the D is piperidino, R'₁ is hydroxy; and Ar is phenyl substituted by one or two halo, alkyl, alkoxy or trifluoromethyl in which halo is chloro or fluoro; or
wherein D is 1,2,5,6-tetrahydropyridino, R'₁ is absent and Ar is phenyl or phenyl substituted with one or two halo, alkyl, alkoxy, or trifluoromethyl groups, wherein halo, alkyl and alkoxy are as defined above; or the pharmacologically acceptable acid addition salts thereof.

25. A method according to claim 23 wherein the compound is of the formula IIB

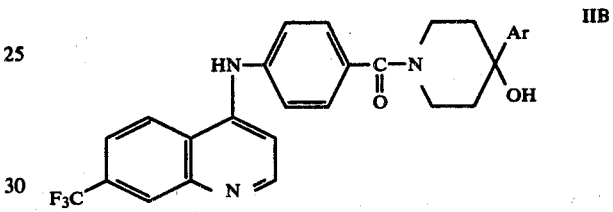

wherein Ar is phenyl substituted by one or two halo, alkyl, alkoxy, or trifluoromethyl groups in which halo is chloro or fluoro and alkyl and alkoxy are from 1 to 3 carbon atoms; or the pharmacologically acceptable acid addition salts thereof.

26. A method according to claim 24 wherein the compound is 4-(4-chlorophenyl)-1,2,5,6-tetrahydro-1-[4-[[7-(trifluoromethyl)-4-quinolinyl]amino]benzoyl]pyridine.

27. A method according to claim 24 wherein the compound is 4-(3-trifluoromethylphenyl)-1,2,5,6-tetrahydro-1-[4-[[7-(trifluoromethyl)-4-quinolinyl]amino]benzoyl]pyridine.

28. A method according to claim 25 wherein the compound is 4-hydroxy-4-(4-chlorophenyl(-1-[4-[[7-(trifluoromethyl)-4-quinolinyl]amino]benzoyl]piperidine.

29. A method according to claim 25 wherein the compound is 4-hydroxy-4-(3-trifluoromethylphenyl)-1-[4-[[7-(trifluoromethyl)-4-quinolinyl]amino]benzoyl]piperidine.

30. A method according to claim 25 wherein the compound is 4-hydroxy-4-(4-trifluoromethylphenyl)-1-[4-[[7-(trifluoromethyl)-4-quinolinyl]amino]benzoyl]piperidine.

* * * * *

UNITED STATES PATENT OFFICE
CERTIFICATE OF CORRECTION

Patent No. 4,166,853                          Dated 4 September 1979

Inventor(s) John M. McCall

It is certified that error appears in the above-identified patent and that said Letters Patent are hereby corrected as shown below:

Column 7, line 58, "[4-[[71-(trifluoromethyl)" should read
-- [4-[[7-(trifluoromethyl) --;
Column 11, line 59, "Ia the manner" should read -- In the manner --;
Column 15, line 11, "Essential Active ingredient micronized" should
 be followed by -- 10 g --; lines 25-27, "using the procedure of EXAMPLE 35"
should read -- using the procedure of Example 35 --;
Column 17, line 32, "4-(4-chlorophenyl(-4-" should read -- 4-(4-chlorophenyl)-4- --; line 46, "4-[3-(trifluoromethyl(" should read --4-[3-(trifluoromethyl) --; line 46-47, "[4-[[7-(trifluoromethyl(" should read -- [4-[[7-(trifluoromethyl) --;
Column 19, line 9, "4-(4-chlorophenyl(-" should read -- 4-(4-chlorophenyl)- --

*Signed and Sealed this*

*Fifth* Day of *August 1980*

[SEAL]

*Attest:*

SIDNEY A. DIAMOND

*Attesting Officer*     *Commissioner of Patents and Trademarks*